United States Patent [19]
Cline et al.

[11] Patent Number: 5,247,935
[45] Date of Patent: Sep. 28, 1993

[54] MAGNETIC RESONANCE GUIDED FOCUSSED ULTRASOUND SURGERY

[75] Inventors: Harvey E. Cline; Robert H. Ettinger, both of Schenectady; Kenneth W. Rohling, Burnt Hills; Ronald D. Watkins, Niskayuna, all of N.Y.

[73] Assignee: General Electric Company, Schenectady, N.Y.

[21] Appl. No.: 854,040

[22] Filed: Mar. 19, 1992

[51] Int. Cl.⁵ .............................. A61B 5/055
[52] U.S. Cl. ................... 128/653.2; 128/24.1; 128/399; 128/653.5; 128/24 AA
[58] Field of Search ............... 128/653.2, 653.5, 24.1, 128/24 AA, 660.03, 662.03, 662.06, 663.01, 736, 399; 324/318

[56] References Cited

U.S. PATENT DOCUMENTS

| | | | |
|---|---|---|---|
| Re. 33,590 | 5/1991 | Dory | 128/660.03 |
| 4,543,959 | 10/1985 | Sepponen | 128/653.2 |
| 4,567,894 | 2/1986 | Bergman | 128/653.5 |
| 4,617,931 | 10/1986 | Dory | 128/24 AA |
| 4,620,546 | 11/1986 | Aida et al. | 128/660.03 |
| 4,646,756 | 3/1987 | Watmough et al. | 128/804 |
| 4,658,828 | 4/1987 | Dory | 128/660.03 |
| 4,807,633 | 2/1989 | Fry | 128/736 |
| 4,875,485 | 10/1989 | Matsutani | 128/653.5 |
| 4,955,365 | 9/1990 | Fry et al. | 128/660.03 |
| 5,054,470 | 10/1991 | Fry et al. | 128/24 AA |
| 5,109,853 | 5/1992 | Taicher et al. | 128/653.2 |
| 5,131,392 | 7/1992 | Jolesz et al. | 128/653.2 |

FOREIGN PATENT DOCUMENTS

9002343  3/1990  European Pat. Off. ......... 128/653.5

*Primary Examiner*—Lee S. Cohen
*Assistant Examiner*—K. M. Pfaffle
*Attorney, Agent, or Firm*—Lawrence P. Zale; Marvin Snyder

[57] ABSTRACT

A magnetic resonance surgery system facilitates performance of surgery with a focussed ultrasound transducer that selectively destroys tissue in a region within a subject. The focussed ultrasound transducer dissipates ultrasonic energy at a focal point within the region of tissue to be destroyed. A number of hydraulic positioners position the focal point under the control of a surgeon. A magnetic resonance imaging system employing a temperature sensitive pulse sequence creates an image of the tissue and the region being heated to allow the surgeon to adjust the position of the ultrasonic transducer so as to direct ultrasonic energy to the appropriate location.

4 Claims, 10 Drawing Sheets

MAGNETIC RESONANCE GUIDED FOCUSSED ULTRASOUND SURGERY

CROSS REFERENCES

This application is related to U.S. Patent Application MAGNETIC RESONANCE SURGERY USING HEAT WAVES PRODUCED WITH A LASER FIBER OR FOCUSSED ULTRASOUND by Dr. Harvey E. Cline and Thomas R. Anthony et al. Ser. No. 07/751,259 filed Aug. 29, 1991, assigned to the present assignee and hereby incorporated by reference.

BACKGROUND OF THE INVENTION

The present invention relates to a system for enabling surgery to be performed by vibrational heating and more particularly to a system for enabling surgery to be performed by ultrasonic heating guided by magnetic resonance (MR) imaging.

Conventional Magnetic Resonance Imaging (MRI) provides the radiologist with internal views of a subject's anatomy. MRI provides excellent contrast between different tissues and is useful in planning surgical procedures. A tumor in a subject is much more visible in an MR image than as seen in actual surgery because the tumor and normal tissue often look similar in surgery. The tumor can also be obscured by blood during surgery. Researchers at Brigham and Womens Hospital, Boston, Mass. have proposed treatment of deep lying tumors by laser surgery. F. A. Jolesz, A. R. Bleire, P. Jakob, P. W. Ruenzel, K. Huttl, G. J. Jako, "MR Imaging of Laser-Tissue Interactions", Radiology 168:249 (1989). Thus, in the case of brain tumors, the subject is first scanned in an MRI system to locate the tumor and plan a safe trajectory between the entry and target points. This can be accomplished by a MRI device employing fast scan apparatus such as U.S. Pat. Nos. 4,961,054 Gradient Current Speed-up Circuit for High-speed NMR Imaging System by John N. Park, Otward M. Mueller, and Peter B. Roemer, issued Oct. 2, 1990, or 5,017,871 Gradient Current Speed-up Circuit for High-speed NMR Imaging System, by Otward M. Mueller, and Peter B. Roemer, issued May 21, 1991 both assigned to the present assignee and hereby incorporated by reference. A view of the heated region is provided with the use of MR temperature sensitive pulse sequences. Known MR temperature sensitive pulse sequences are described in U.S. Pat. No. 4,914,608 In-vivo Method for Determining and Imaging Temperature of an Object/Subject from Diffusion Coefficients Obtained by Nuclear Magnetic Resonance, Denis LeBihan, Jose Delannoy, and Roland L. Levin issued Apr. 3, 1990. Experiments on animals show that a heated zone above a critical temperature destroys tissue. This zone increases in size with time as the heat is applied to reach a steady state or both temperature and heat flow. If the maximum temperature is limited to 100 deg. C., then the heated zone, the area exceeding a critical temperature causing destruction of tissue, approaches 1 centimeter in diameter. It is difficult to predict the heated zone geometry because the heat flow depends on the profusion of blood as well as the tissue thermal properties.

Tumors have been selectively destroyed in cancer subjects using focused ultrasound heating at the University of Arizona, as reported by B. E. Billard, K. Hynynen and Robert. B. Roemer Effects of Physical Parameters on High Temperature Ultrasound Hyperthermia Ultrasound in Med. & Biol. Vol. 16, No. 4, pp. 409–420, 1990 and hereby incorporated by reference. Billard et al. disclose that the control of heat is improved by using short heating pulses where the effect of blood perfusion is negligible. However, since they do not image the temperature distribution, it is difficult to hit small, deep laying targets.

It would be beneficial to be able to accurately localize heat to selectively kill or destroy tumor tissue without damage to surrounding healthy tissue.

OBJECTS OF THE INVENTION

It is an object of the present invention to position focused ultrasound equipment guided by magnetic resonance imaging.

It is another object of the present invention to selectively destroy tumors with a small amount of invasiveness.

SUMMARY OF THE INVENTION

Pulsed heat from focussed ultrasound equipment is positioned to selectively destroy tumor tissue of a subject with minimal invasiveness by employing magnetic resonance (MR) imaging apparatus to provide, to a surgeon performing the procedure, images of a region within the subject being heated, such region including the tumor tissue. Fast scan MR images are used to monitor the tissue temperature with a diffusion sensitive pulse sequence. The ultrasound transducer concentrates heat at its focus which is positioned on the tumor. The focal point is positioned by a number of hydraulic positioners responsive to a control unit operated by the surgeon.

BRIEF DESCRIPTION OF THE DRAWINGS

The features of the invention believed to be novel are set forth with particularity in the appended claims. The invention itself, however, both as to organization and method of operation, together with further objects, may best be understood by reference to the following description taken in conjunction with the accompanying drawing in which:

DETAILED DESCRIPTION OF THE INVENTION

Tumor tissue in a subject can be selectively destroyed by localized heating without affecting the surrounding healthy tissue. A method of controlling the size of a region being heated by pulsing a heat source is disclosed in Thermal Diffusity of Isotopically Enriched $^{12}C$ Diamond by T. R. Anthony, W. F. Banholzer, and J. F. Fleischer Phys. Rev. B Vol. 42, No. 2 Jul. 15, 1990, hereby incorporated by reference. Similarly, in the present invention heat is applied to the tumor tissue in a pulsed or oscillating fashion. This oscillation creates a heat wave at the focus point of the transducer. The pulsed heat is produced by an ultrasonic energy source driven in accordance with a sinusoidal component and a constant component, and thus varies sinusoidally. However, the constant heating from the heated focus point source steadily adds to the background thermal distribution.

Figure 1:
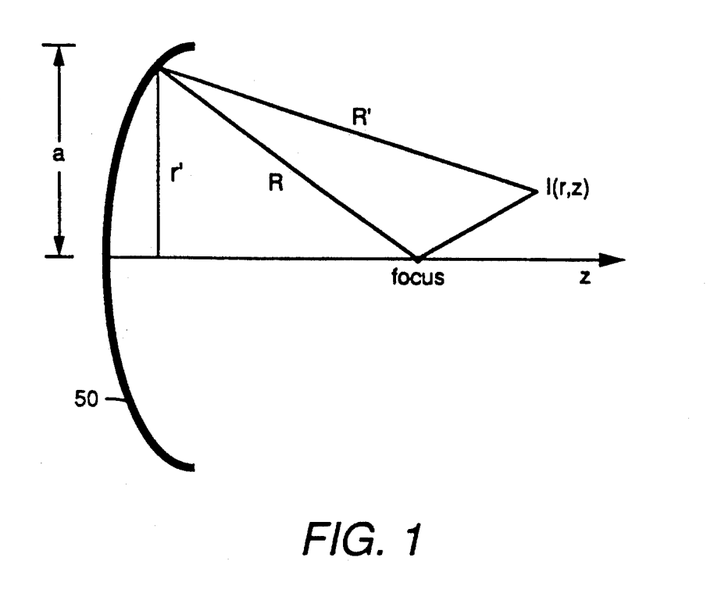
FIG. 1 is a graphical illustration of the heating geometry of an ultrasound transducer.

The heat distribution in focussed ultrasound therapy depends on the intensity distribution $I(r,z)$ in the region near the focus created from a spherical lens of an energy transducer 50 of radius R and diameter $2a$ as shown in FIG. 1. A pressure wave with unit amplitude at the spherical surface is created by superposition of spherical wavelets of the form $Exp(-ikR')/R'$ over the transducer surface according to:

$$P(r, z) = ik \int \frac{Exp(-ikR')}{R'} dS \quad (1)$$

where $dS = R^2 \sin(a) \, da$, $i = \sqrt{-1}$, $k = 2\pi/\lambda$, $R'$ is the distance from a point on the transducer to the point where the intensity $I(r,z)$ is measured, and $\lambda$ is the wavelength of sound. At the focus $R' = R$, the pressure becomes $$P(0, 0) = ikR Exp(-kR) \left[ 1 - \sqrt{1 - \left(\frac{a}{R}\right)^2} \right] \quad (2)$$

and the intensity becomes:

$$I_0 = \left\{ kR \left[ 1 - \sqrt{1 - \left(\frac{a}{R}\right)^2} \right] \right\}^2 \quad (3)$$

which for small apertures $a << R$ becomes approximately:

$$I_0 = \left(\frac{ka^2}{2R}\right)^2 \quad (4)$$

Figure 2:
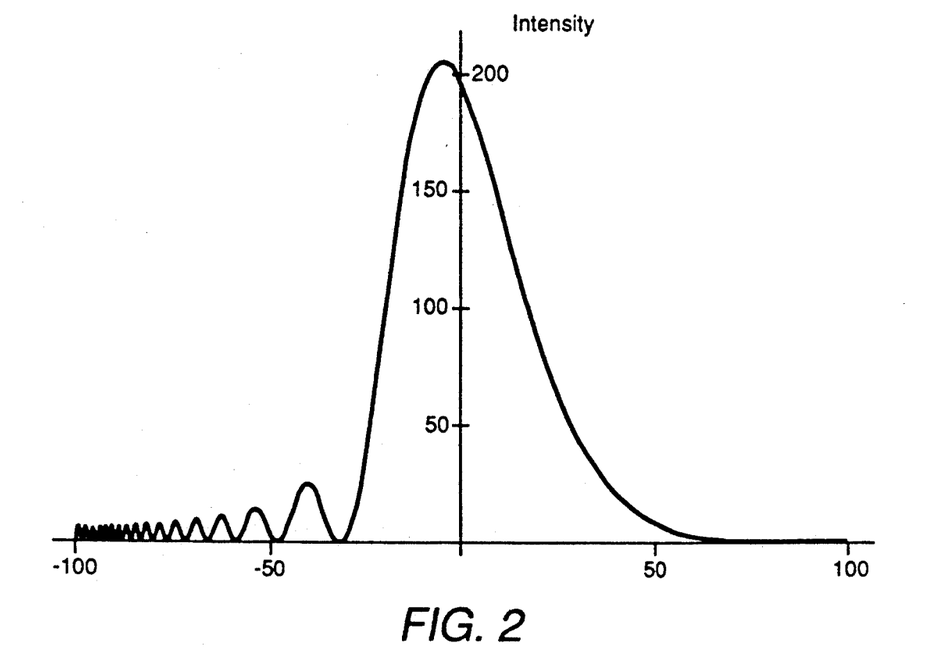
FIG. 2 is a heat intensity profile of an ultrasound transducer having a 5 cm. diameter, the intensity being measured along an axis passing through the center of an ultrasound transducer and through its focal point.

FIG. 2 is a graph of the ultrasonic signal intensity along the axis of a 5 cm. diameter spherical transducer operating at 1.1 MHz, calculated by integrating Eq. (1). An intensity maximum occurs at a broad asymmetric central peak being 210 times the intensity at the transducer surface. However, by increasing the diameter of a 1.1 MHz. transducer from 5 cm. to 10 cm., the calculated peak becomes narrow with a maximum value 3500 times the intensity at the transducer, as shown in FIG. 3.

Figure 3:
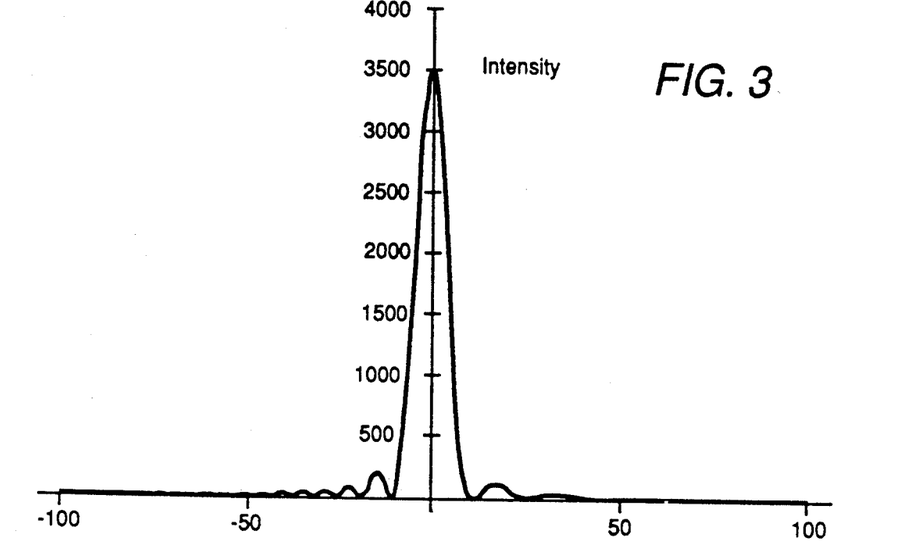
FIG. 3 is a heat intensity profile of an ultrasound transducer having a 10 cm. diameter, the intensity being measured along an axis passing through the center of an ultrasound transducer and through its focal point.
Figure 4:
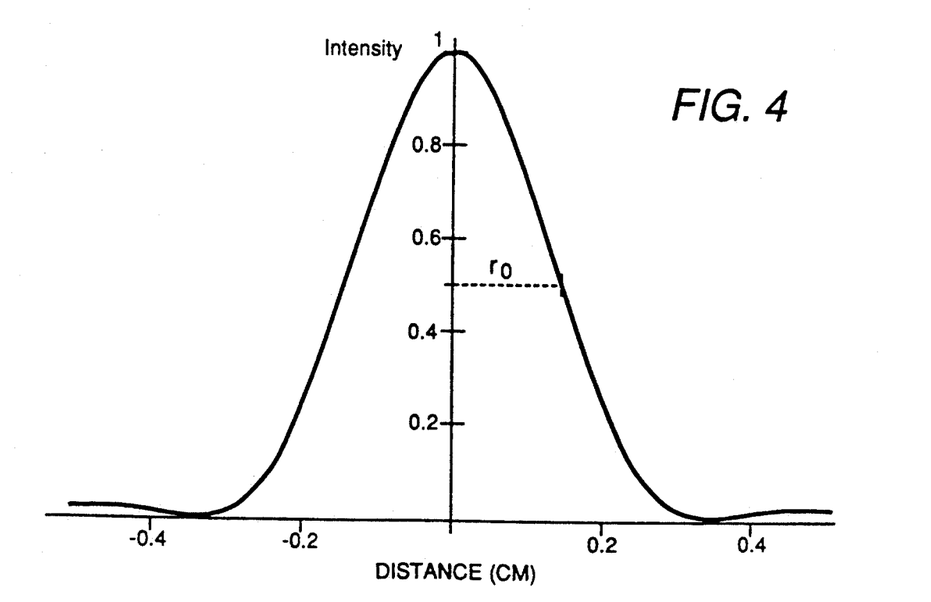
FIG. 4 is a heat intensity profile along an axis perpendicular to the axis of FIG. 3.

FIG. 4 shows the fraction of maximum signal intensity in a focal plane perpendicular to the axis of FIG. 3. The width of the graph of FIG. 4 measured at an intensity which was ½ the maximum intensity, $r_0$, is known as the diffraction limited width of the transducer. This width, $r_0$, was calculated to be 0.25 cm.

A energy transducer pulsed at a frequency f creates a heated region having a size and temperature distribution T described by:

$$T(r,t) = [Q/\rho c \, Exp[-kr] \cos(2\pi ft - kr)]/r \quad (5)$$

where r is the radius from the center of the heated region;

t is time;

$\rho$ is density of the heated region;

c is specific heat of the heated region; and $$k = \sqrt{\frac{\omega}{2D}} \, .$$

where D is the thermal diffusity of the tissue in the heated region, and $\omega$ is the angular frequency.

For a further description of the pulsed heat distribution, refer to the aforementioned U.S. patent application Ser. No. 07/751,259, Cline, et al, filed Aug. 29, 1991.

Figure 5:
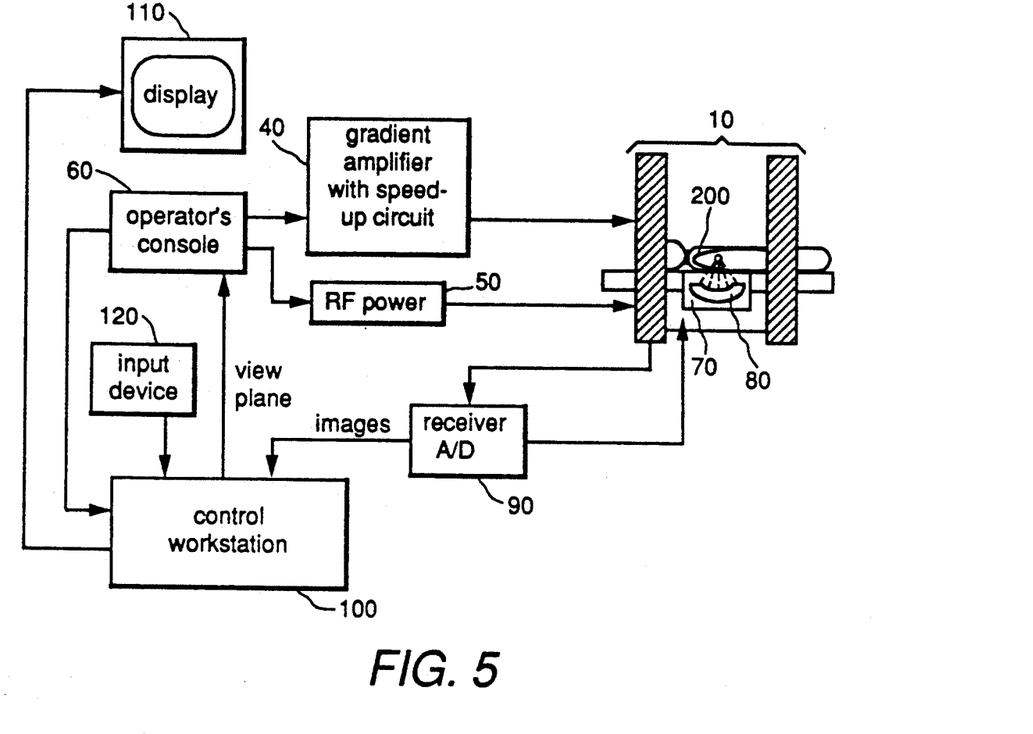
FIG. 5 is a schematic block diagram of the present invention.

A schematic block diagram of the magnetic resonance surgery system is shown in FIG. 5. A magnetic resonant imaging system 10 employs pulse sequences in the well known manner to rapidly acquire images of a subject 200. A gradient amplifier 40 and an rf power source 50 supply the power for the sequences. An operator console 60 is used to control the imaging system. Raw data is sent from receiver 90 to a control workstation 100 that displays images 110 to a surgeon. Control workstation 100 computes a path to a desired location within subject 200 from transducer 80 which avoids bone and air spaces. The surgeon indicates the desired location of the focal point of ultrasound transducer 80 by means of an input device 120 which can be a three-dimensional pointing device such as a track ball or a mouse. Control workstation 100 actuates positioning means 70 to position ultrasound transducer 80. Magnetic resonant imaging system 10 then employs pulse sequences to rapidly acquire temperature sensitive images of subject 200. Since both the internal structures and heated regions are imaged, the surgeon can accurately position the heated region to correspond to a desired internal structure through input device 120.

Figure 6:
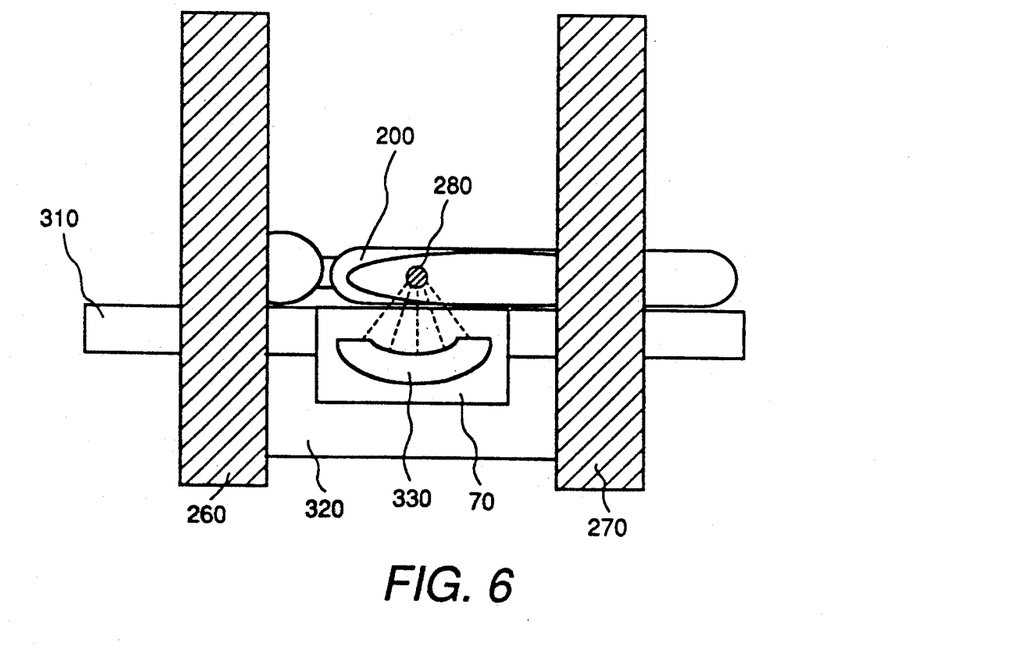
FIG. 6 is an illustration of a subject positioned for surgery within the bore of the magnets of an MRI system employed in the present invention.

As shown in FIG. 6, subject 200 is placed on a table 310 designed to accommodate a focussed ultrasound transducer 330 in an ultrasound conducting liquid bath 320. The ultrasound conducting liquid chosen is one that will conduct ultrasonic energy with little attenuation. The ultrasound transducer 330 can be moved inside the bore of magnets 260, 270 by positioning means 70 to focus on different locations within subject 200. A path is computed by control workstation 100 from a set of images of the subject taken during surgery planning avoiding bone or air in the path of the ultrasound beam. The focal point of ultrasound transducer 330 is positioned along the computed path by positioning means 70 onto a tumor 280 and pulsed according to equation (5) to selectively heat tumor 280. The ultrasound transducer is moved while the surgeon views cross sectional temperature sensitive images.

Figure 7:
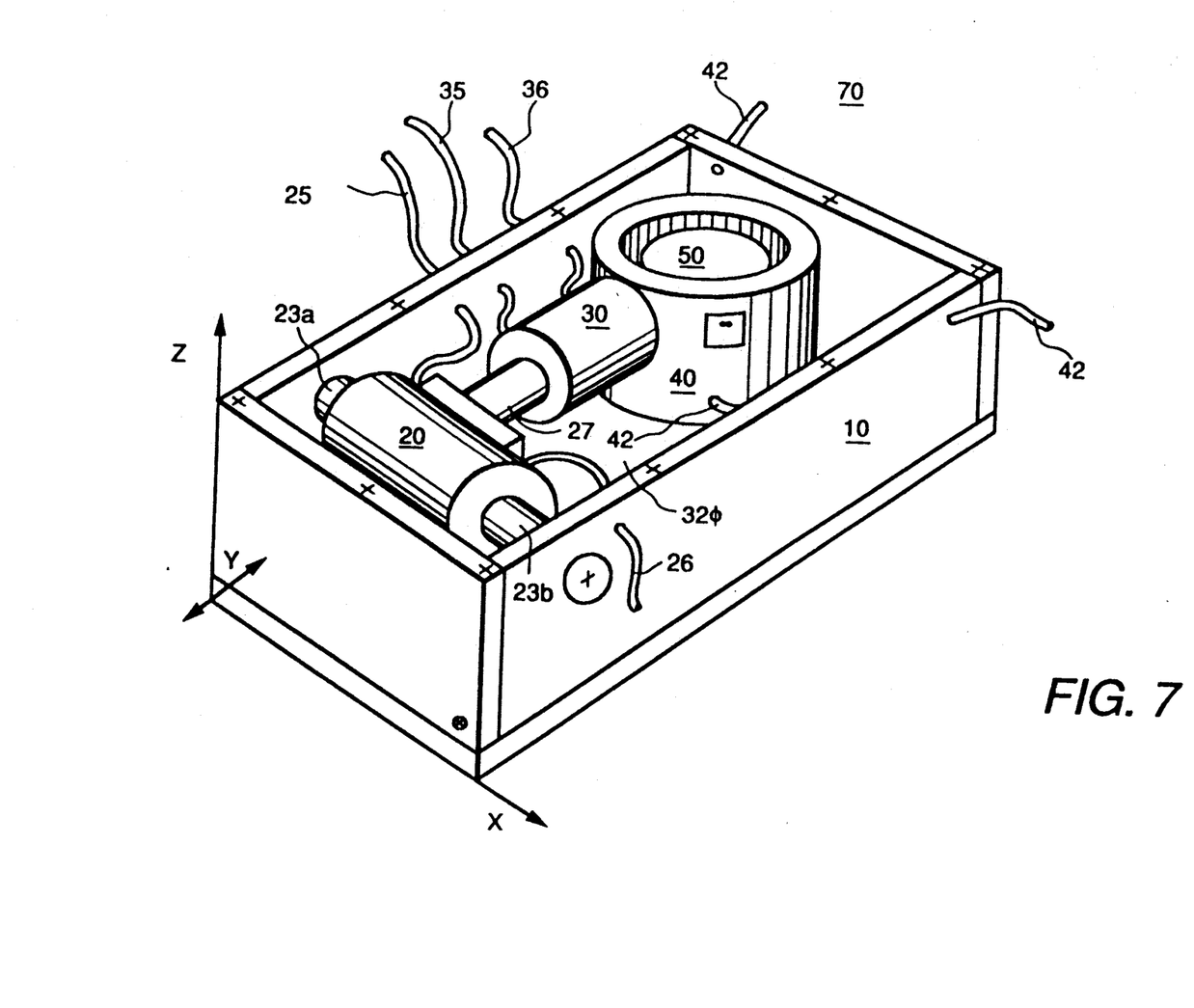
FIG. 7 is an partial illustration of a positioning means showing an ultrasound transducer and hydraulic positioners according to one embodiment of the present invention.

FIG. 7 shows an ultrasonic transducer 50 connected to a partial assembly of the positioning means. The positioning means is comprised of a casing 10 which encloses an ultrasound transmitting fluid 320, which is preferably water, and a number of hydraulic positioners 20, 30, 40. All materials of positioning means 70 are non-metallic and non-magnetic in order to minimize any interference with the magnetic resonance imaging system.

The first hydraulic positioner 20 is connected to hydraulic lines 25 and 26 through which a pressurized hydraulic fluid is pumped to and from positioner 20. Positioner 20 causes motion of positioners 30, 40 and ultrasonic transducer 50 in the x direction.

Positioner 30 which is situated between, and affixed to, positioner 20 and positioner 40 has hydraulic fluid pumped to and through it from hydraulic lines 35 and 36. Positioner 30 causes motion of positioner 40 and ultrasound transducer 50 in the y direction.

Positioner 40 has hydraulic fluid pumped to and from it through hydraulic line 42 and causes motion of the ultrasound transducer 50 in a z direction.

Figure 8:
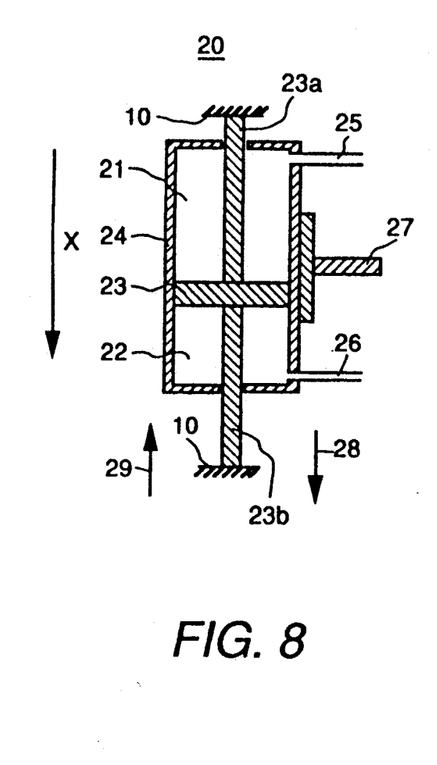
FIG. 8 is a cutaway illustration of a first positioner of the present invention.

FIG. 8 is a cut-away illustration of positioner 20. Positioner 20 has a housing 24 in which a piston 23 is fitted. Piston 23 creates a fluid-tight seal between itself and housing 24, creating two chambers 21 and 22. Piston 23 has two extensions, 23a and 23b, which are secured to casing 10 of the positioning means shown in FIG. 7. Hydraulic fluid is pumped into chamber 21 through hydraulic line 25, causing housing 24 to move in the direction marked by arrow 29. This causes fluid in chamber 22 to exit through hydraulic line 26. Conversely, when fluid is pumped in through hydraulic line 26 into chamber 22, housing 24 moves in the direction marked by arrow 28, causing fluid in chamber 21 to exit through hydraulic line 25. Structure 27 is affixed to housing 24 and moves in the same direction as housing 24.

Figure 9:
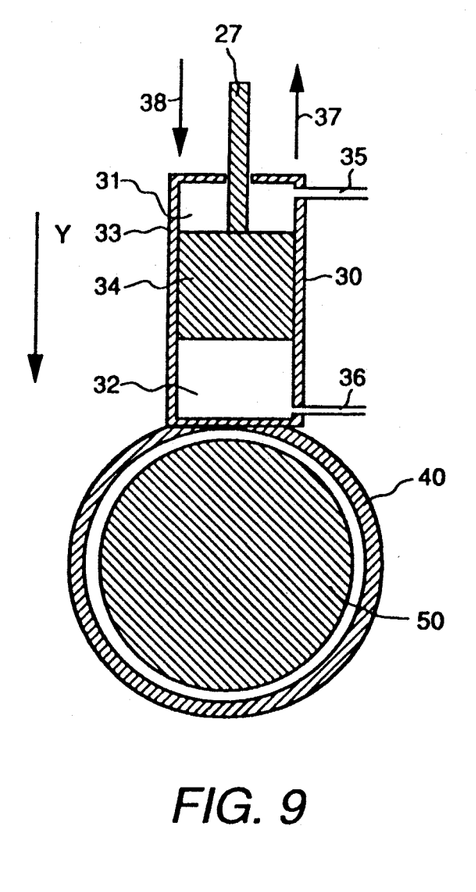
FIG. 9 is a cutaway illustration of a second positioner and ultrasound transducer of the present invention.

FIG. 9 is a cut-away illustration of positioner 30 attached to positioner 40 and ultrasound transducer 50. Positioner 30 has a housing 33 which encloses piston 34, creating chambers 31 and 32. Structure 27, affixed to piston 34, is also affixed to positioner 20 of FIGS. 7 and 8. As hydraulic fluid enters through hydraulic line 35, housing 33, positioner 40 and ultrasound transducer 50 move in a direction marked by arrow 37. When hydraulic fluid enters chamber 32 through hydraulic line 36, hydraulic fluid exits chamber 31 through hydraulic line 35 causing motion of housing 33, positioner 40 and ultrasound transducer 50 in a direction marked by arrow 38. Directions 37 and 38 are parallel to the y-axis as shown in FIG. 7.

Figure 10:
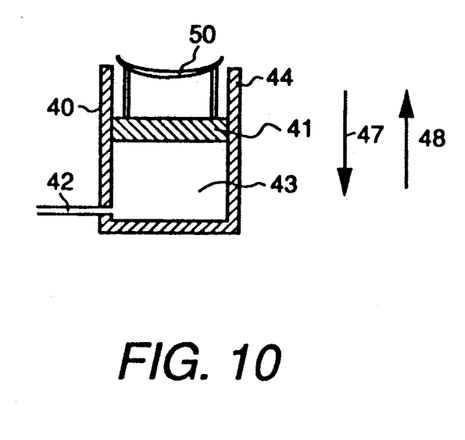
FIG. 10 is a cutaway illustration of a third positioner and ultrasound transducer of the present invention.

In FIG. 10 positioner 40 and ultrasound transducer 50 are shown in a cut-away view. Transducer 50 is mounted on piston 41 which creates a fluid-tight seal with housing 44. Chamber 43 receives hydraulic fluid through hydraulic line 42, causing motion along z-axis as shown by arrow 48. As fluid is pumped from chamber 43 through hydraulic line 42, piston 41 and ultrasound transducer move in a direction marked by arrow 47.

Figure 11:
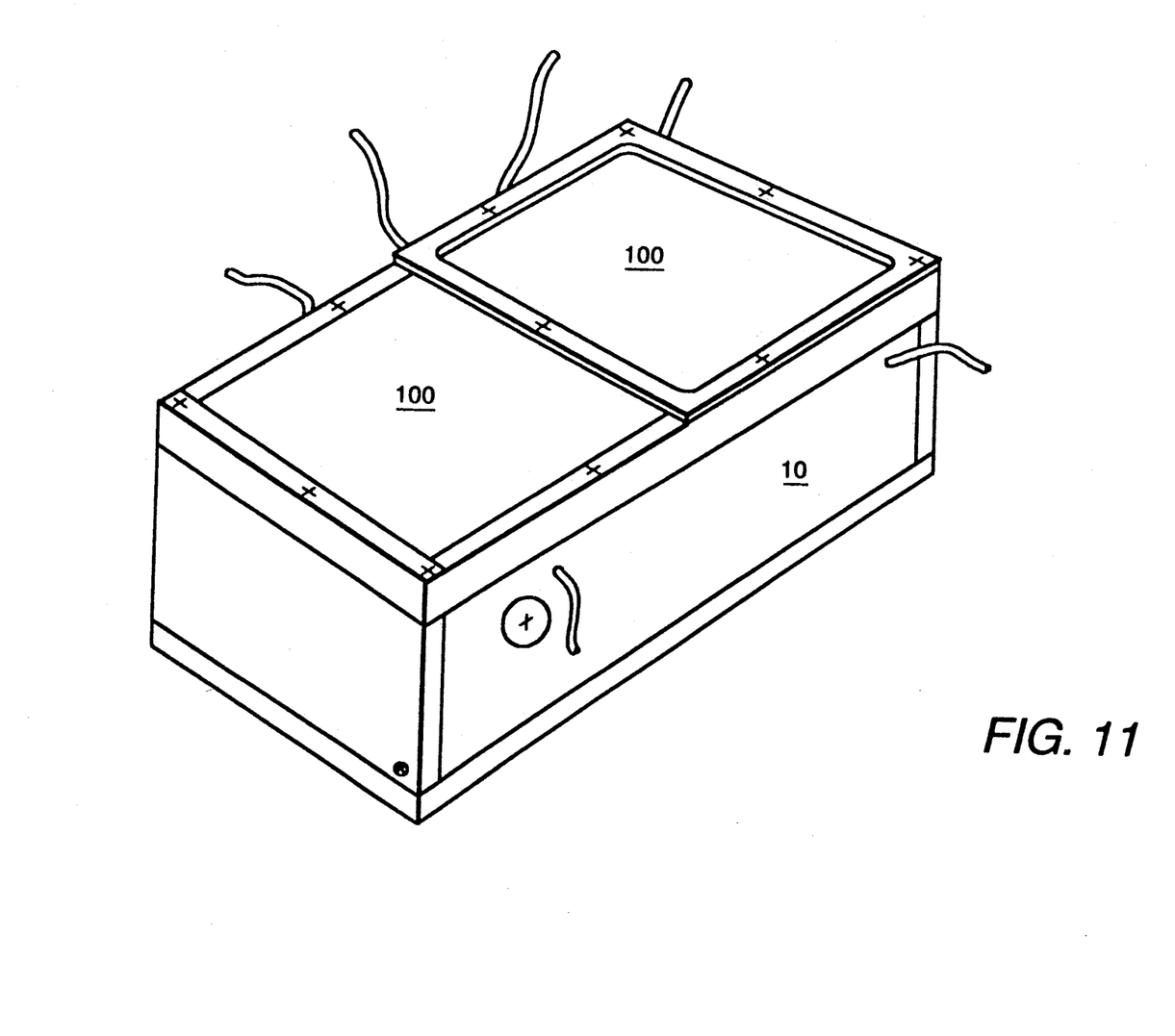
FIG. 11 is an illustration of the positioning means of FIG. 7 with its interface window attached.
Figure 12A:
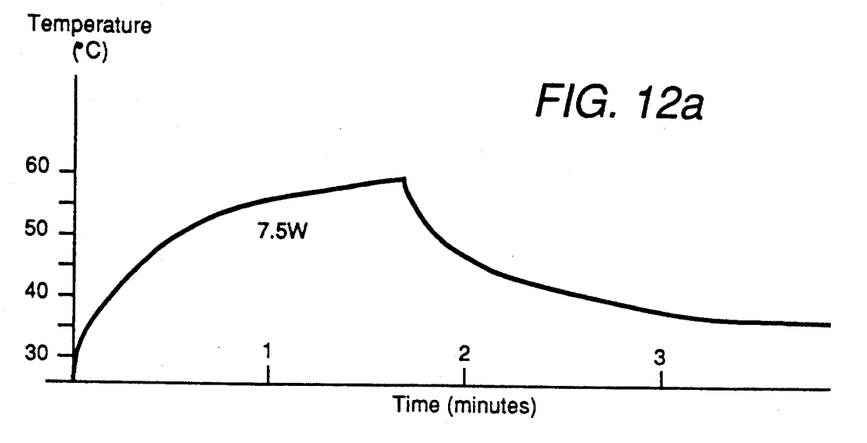
FIGS. 12a-12e are each a graph of the heating and cooling characteristics operating an ultrasound transducer at a different power.
Figure 12B:
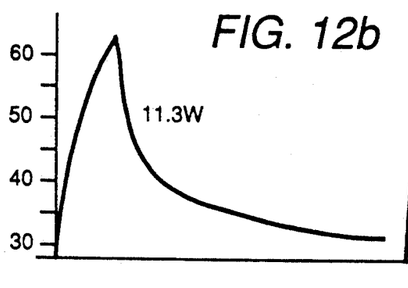
Figure 12C:
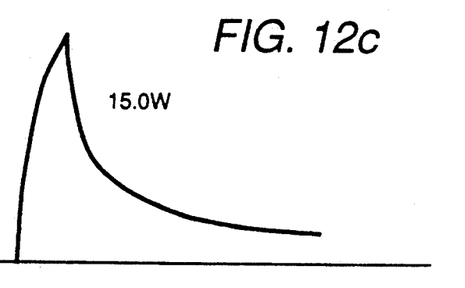
Figure 12D:
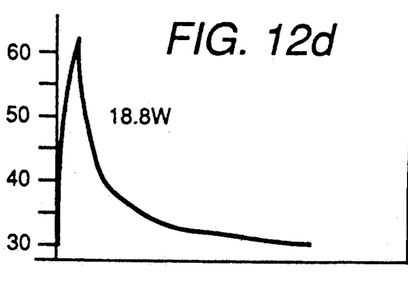
Figure 12E:
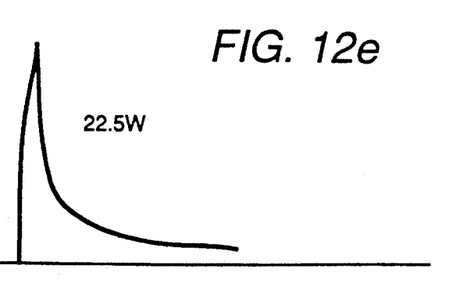

FIG. 11 illustrates the positioning means with a cover 100 and an ultrasound membrane 110 attached to casing 10. The ultrasound membrane 110 is a flexible material which is ultrasound transparent such as a Mylar plastic film diaphragm, a trademark of the E. I. du Pont Nemours and Company, Willmington, Del. Ultrasound membrane 110 is made thin enough to conform to the contours of a subject. The subject is placed on ultrasound membrane 110 with ultrasonic conducting gel extending between the ultrasound membrane and the subject. Energy from ultrasound transducer 50, as shown in FIG. 7, passes through fluid 320, through ultrasound membrane 110, shown in FIG. 11, through the ultrasound gel between ultrasound membrane 110 and into the subject. In order to efficiently transfer the energy, there should be no intervening air spaces between transducer 50 and the subject.

The thermal response of an acoustic silicone gel phantom tested at power levels 30, 45, 60, 75 and 90 watts over the temperature range of 30 to 60 deg C. is illustrated in FIGS. 12a–12e, respectively. A 5 cm diameter 1.1 MHz ultrasound transducer was used. The time for the temperature at the focal spot to reach 60 deg C. at different applied power levels is given in Table 1. This time decreased with increasing applied power, as would be expected.

TABLE 1

| power (watts) | rise time from 30-60C (sec) | ave heating rate (deg C/sec) | energy (joules) | absorbed heat q (watts cm) | calculated attenuation (cm$^{-1}$) |
|---|---|---|---|---|---|
| 90 | 4 | 7.5 | 360 | 4.4 | .049 |
| 75 | 8 | 3.8 | 600 | 2.7 | .036 |
| 60 | 12 | 2.7 | 720 | 2.0 | .033 |
| 45 | 33 | 1.0 | 1500 | 1.2 | .027 |
| 30 | 100 | 0.3 | 3000 | 0.8 | .027 |

Figure 13:
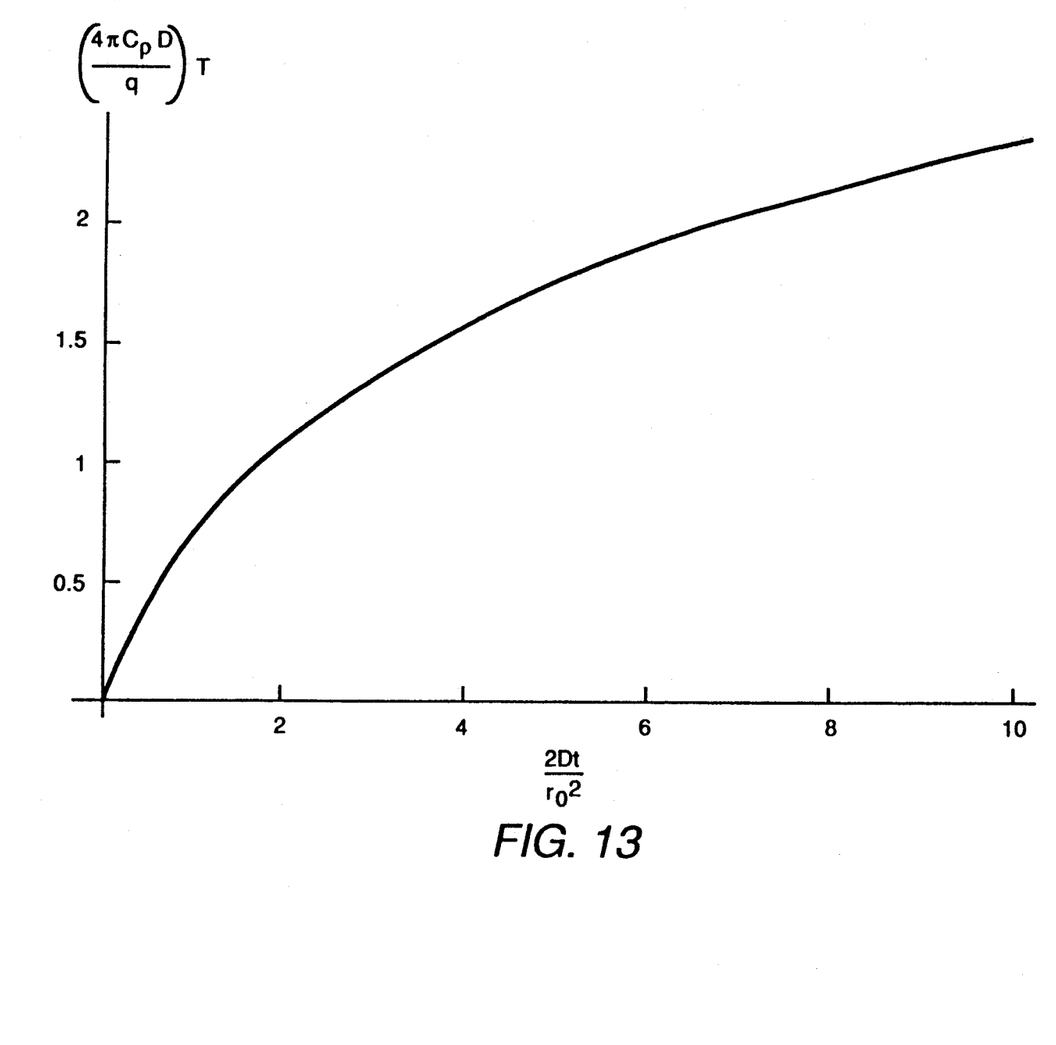
FIG. 13 is a graph of the temperature increase over time for a specific transducer and tissue.

The transient heating curve was obtained using the same phantom and transducer as above. The curve is shown in FIG. 13, with the horizontal axis being a constant $$\left( \frac{4\pi C_p D}{q} \right)$$

multiplied by time t, and the vertical axis being a constant $$\frac{2D}{r_0^2}$$

multiplied by temperature T. $C_p$ is the volume specific heat and $r_0$ is the width of the ultrasound beam in a plane perpendicular to a line through the center of the transducer and focal point. This width is measured at an amplitude being ½ the maximum amplitude. The curve of FIG. 13 is in agreement with a thermal model of a continuous line source given by:

$$T(0, t) = \frac{q}{4\pi\kappa} \ln\left[1 + \frac{2Dt}{r_0^2}\right] \quad (6)$$

where $\kappa$ is the thermal conductivity.

At higher power levels both the rate of heating and cooling are faster. More energy is used at lower power levels because there is more time for the heat to diffuse; consequently, it takes more time for the material to cool down, After the heat pulse of duration D is turned off, the temperature at focus becomes $$T(0, t) = \frac{q}{4\pi\kappa} \ln\left\{\frac{\left|1 + \frac{2Dt}{r_0^2}\right|}{\left|1 + \frac{2D|t - \Delta|}{r_0^2}\right|}\right\} \quad (7)$$

where $\Delta$ is the duration of heat application.

The absorbed heat along the line source increases with applied power. A calculated attenuation is found by obtaining the ratio of the absorbed heat per unit length and the applied power in the beam. The heat absorbed for a 0.13 cm. radius Gaussian source in a material with a diffusivity of 0.0015 cm²/sec is found from our thermal analysis to be related to the pulse duration by:

$$q = 2.4/\ln[1 + 0.18\ t] \quad (8)$$

where q is the absorbed heat per unit length at the focus, assuming an elongated focal spot.

Figure 14A:
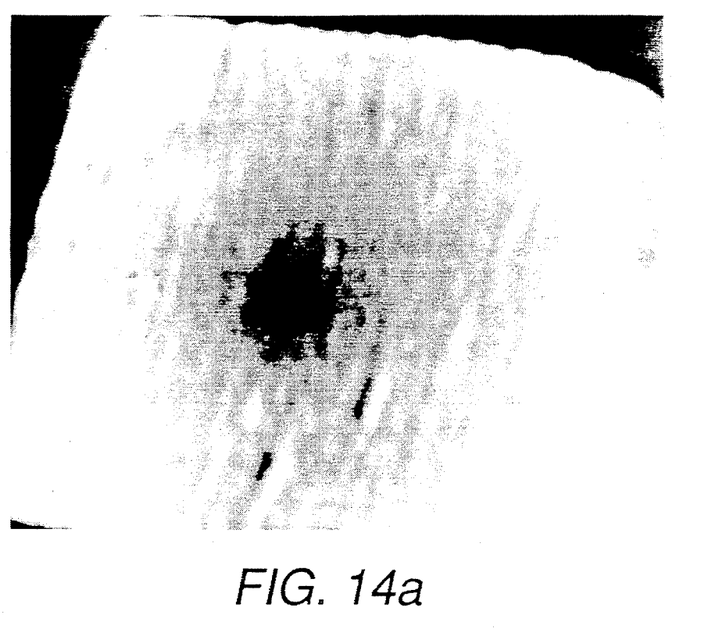
FIGS. 14a-14d are MR images illustrating the effects of ultrasonic heating on an in-vitro beef sample.
Figure 14B:
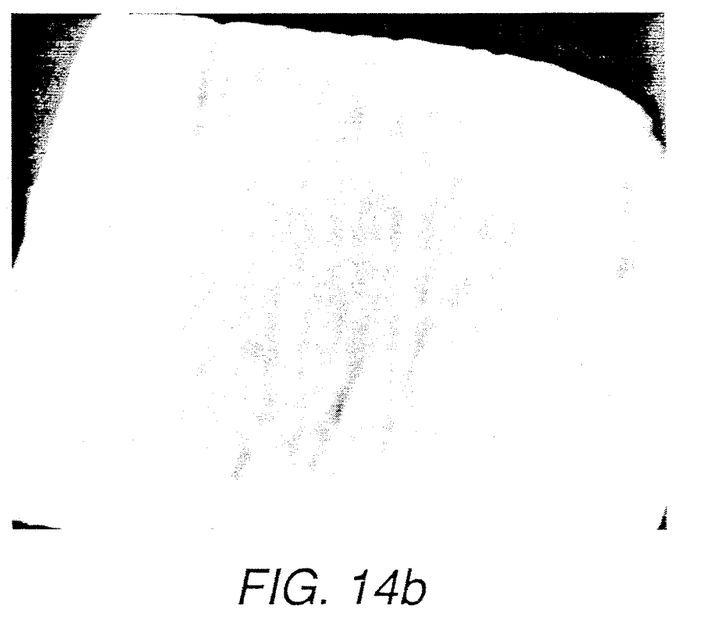
Figure 14C:
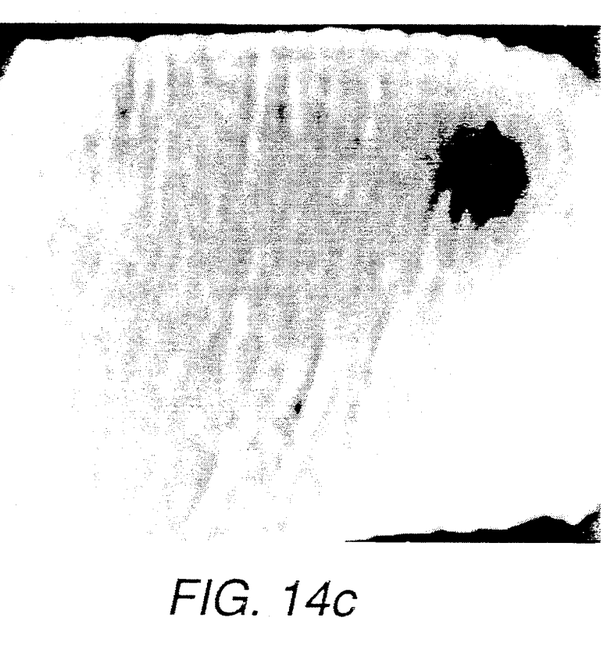
Figure 14D:
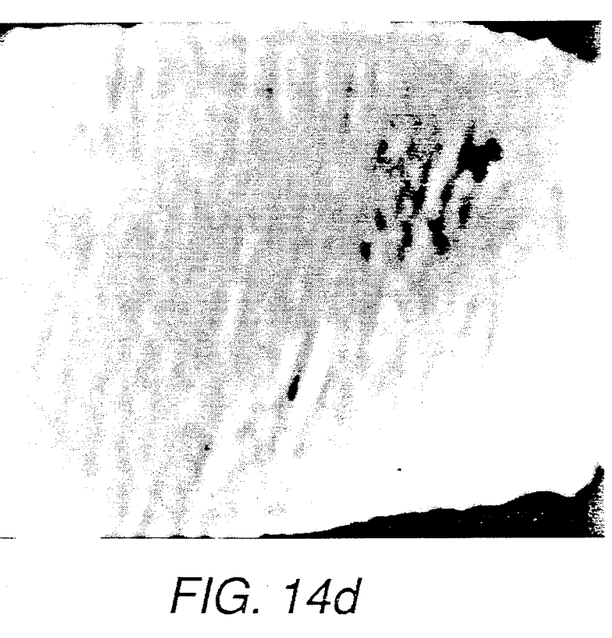

In FIG. 14a an MR image of a portion of an in-vitro excised beef sample that was heated with 100 watts of applied ultrasonic power for 3 min while acquiring a spin echo image of the focal plane is shown. A dark circular spot appeared at the focus. When the ultrasonic heating was terminated the dark spot dissipated indicating that there was no tissue damage as shown in FIG. 14b. Next the transducer focus was moved to another location and the sample was heated. Another dark spot appeared on the MR image indicating the heat zone as shown in FIG. 14c. The applied power was then increased to 150 watts at which level the temperature reached 60 deg C. At this temperature the region at the focus was irreversibly changed. A small dark circle about 2 mm. at the focus appeared and remained on the image after the heating was discontinued as shown in FIG. 14d. Upon examination of the meat sample the tissue was found to have been destroyed at the focal spot, verifying the indication provided by the MR image.

While several presently preferred embodiments of the invention have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance pulsed heat system for selectively heating a region of a subject, comprising:
   a) a magnetic resonance imaging system for imaging internal structures of said subject and for creating temperature sensitive images of such structures during surgery;
   b) an energy transducer for focussing ultrasonic energy to create a heated region within the subject;
   c) an ultrasonic energy conductive interface means for placing between said subject and the energy transducer;
   d) control means for receiving from an operator location information regarding a desired position of the heated region relative to said internal structures and responsive to said magnetic resonance imaging system for receiving information regarding actual position of the heated region relative to said internal structures, said control means further being coupled to said transducer;
   e) non-magnetic positioning means coupled to the energy transducer and the control means, the positioning means comprising a plurality of interconnected hydraulic positioners each being responsive to the control means for positioning the heated region in accordance with the location information regarding the desired position; and
   f) means responsive to said control means for displaying the structures and temperature sensitive images to the operator to enable the operator to control the position and size of the heated region.

2. The magnetic resonance pulsed heat system of claim 1 wherein the energy transducer comprises an ultrasound transducer, and the interface means comprises:
   a) an ultrasound transparent membrane adapted for contact with the subject;
   b) an ultrasound transparent medium in contact with the membrane and situated between the membrane and the transducer, for conducting ultrasound energy from the transducer to the membrane.

3. The magnetic resonance pulsed heat system of claim 1 wherein the control means comprises:
   a) an input device allowing the operator to choose a three-dimensional position for said transducer; and
   b) a control workstation coupled to the input device and the positioning means for converting the chosen three-dimensional position to a position signal for driving the positioning means.

4. The magnetic resonance pulsed heat system of claim 1 wherein each hydraulic positioner of the non-magnetic positioning means is aligned to cause motion of the energy transducer in a different respective direction, each hydraulic positioner comprising:
   a) a casing;
   b) a piston fitted in the casing;
   c) at least one piston chamber between the casing and the piston;
   d) at least one lead tube connected to the at least one chamber; and
   e) pressurized hydraulic fluid within the at least one lead tube for activating the piston.

* * * * *